United States Patent [19]

Wilczek

[11] Patent Number: 5,233,071
[45] Date of Patent: Aug. 3, 1993

[54] HYDROSILATION OF FLUORINATED OLEFINS WITH COBALT CATALYSTS

[75] Inventor: Lech Wilczek, Wilmington, Del.

[73] Assignee: E. I. Du Pont de Nemours and Company, Wilmington, Del.

[21] Appl. No.: 852,461

[22] Filed: Mar. 17, 1992

[51] Int. Cl.$^5$ ................................................ C07F 7/08
[52] U.S. Cl. .................................... 556/479; 556/437; 556/439; 556/440; 556/452; 556/453; 556/457; 556/460
[58] Field of Search ............... 556/479, 440, 439, 437, 556/452, 453, 457, 460

[56] References Cited

U.S. PATENT DOCUMENTS 3,714,212  1/1973  Lengnick ............................ 556/479

OTHER PUBLICATIONS

I. Ojima, et al., *J. Organometal. Chem.*, vol. 260, pp. 335–346 (1984).
J. F. Harrod et al., *J. Am Chem. Society*, 87, 16, Communications to the Editor, p. 1133 (1965).

*Primary Examiner*—Paul F. Shaver
*Attorney, Agent, or Firm*—Barbara C. Siegell

[57] ABSTRACT

Alpha-fluorinated olefins are hydrosilated using selected cobalt compounds as catalysts. The products are useful in coatings, and as chemical intermediates, elastomers, and caulks.

18 Claims, No Drawings

HYDROSILATION OF FLUORINATED OLEFINS WITH COBALT CATALYSTS

BACKGROUND OF INVENTION

This invention concerns a process for the hydrosilation of alpha-fluorinated olefins, in which selected cobalt compounds are used as catalysts.

The hydrosilation of olefins is a powerful and versatile method for the synthesis of various silicon compounds. Hydrosilation reactions using various silicon hydride and olefin combinations are known to be catalyzed by a variety of selected metal compounds, and in particular certain of the Group VIII metals have been found to be especially useful.

The hydrosilation of alpha-fluorinated olefins has been carried out using several Group VIII metal compounds [see for example I. Ojima, et al., J. Organometal. Chem., vol. 260, p. 335-346 (1984)].

However, in many of these reactions relatively poor yields of the simple hydrosilation product and/or relatively large amounts of other byproducts are obtained. It is believed that the highly electron withdrawing nature of the fluorine atom makes hydrosilation of alpha-fluorinated olefins difficult.

Cobalt compounds are known to effect hydrosilation of simple (unfluorinated) olefins, see for example J. F. Harrod and A. J. Chalk, J. Am. Chem. Soc., vol. 87, p. 1133 (1965). However, the hydrosilation of alpha-fluorinated olefins using cobalt compounds was not reported.

SUMMARY OF THE INVENTION

This invention concerns a process for the hydrosilation of alpha-fluorinated olefins, comprising, contacting a silicon hydride with an olefin of the formula $H_2C=CHCFR^1R^2$ and a catalytically effective amount of catalyst of the formula $Co_2(CO)_{8-z}L_z$, wherein:

$R^1$ is fluorine or perfluorohydrocarbyl;

$R^2$ is fluorine, hydrogen, hydrocarbyl, or substituted hydrocarbyl;

z is 0 or an integer of 1 to 7;

each L is independently CO, $PR^3_3$ or $P(OR^4)_3$;

$R^3$ is hydrocarbyl;

$R^4$ is hydrocarbyl; and provided that when L is $PR^3_3$, only one or two of $R^3$ is aryl.

DETAILS OF THE INVENTION

The basic hydrosilation reaction which the process accomplishes may typically be represented by the equation

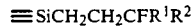

The olefins used in the instant process are fluorinated in the alpha position, that is, there is at least one fluorine atom attached to the carbon atom bound to a vinylic carbon atom. In preferred olefins, $R^1$ is perfluoroalkyl and $R^2$ is fluorine. In especially preferred olefins, $R^1$ is perfluoro-n-alkyl containing 2 to 20 carbon atoms and R2 is fluorine. In another preferred olefin, $R^2$ is ω-hydro or ω-haloperfluoro-n-alkyl, and $R^1$ is fluorine. Herein "halo" means chloro, bromo, or iodo. By the term "hydrocarbyl" herein is meant a univalent radical containing carbon and hydrogen. By the term "substituted hydrocarbyl" herein is meant a hydrocarbyl radical containing substituents that, with the exception of olefinic and acetylenic bonds, are not reactive under process conditions, and do not interfere with the process. Olefinic and acetylenic bonds present in hydrocarbyl groups may themselves be isomerized and/or hydrosilated during the process. This is desirable in some cases, for example the use of an olefin of the formula $CH_2=CH(CF_2)_bCH=CH_2$, where b is 2 to 20, where one or both olefinic groups are hydrosilated in the process. Suitable substituents include, but are not limited to, fluoro, chloro, bromo, iodo, ether (between hydrocarbyl groups), silyl substituted alkyl (which may itself have a silicon hydride group), and silyl substituted aryl (which itself may have a silicon hydride group). Substituents that contain active hydrogen, such as hydroxy and primary amino, should be avoided.

The cobalt catalysts of the invention are carbonyl complexes. In preferred catalysts z is 0 or 2. It is preferred if each $R^3$ and $R^4$ is independently alkyl containing 1 to 6 carbon atoms, or phenyl, and especially preferred if each $R^3$ and $R^4$ is independently phenyl or methyl. The cobalt compounds are available commercially or can be made by procedures described in A. R. Manning, J. Chem. Soc. (A), p. 1135 (1968).

Another necessary process ingredient is a silicon hydride. By a "silicon hydride" is meant a compound that contains one or more hydrogen atoms bound directly to silicon ($\equiv i-H$). The silicon hydride may have only to silicon one hydrogen atom bound to a silicon atom, may have more than one hydrogen bound to any particular silicon atom, and/or may have more than one silicon atom that has hydrogen bound to it. Any other group that is substantially stable during the process may be bound to the silicon, such as hydrocarbyl, including alkyl, aryl, and cycloalkyl, substituted hydrocarbyl, chloro, bromo, fluoro, alkoxy, aryloxy, acyloxy, and oxysilyl (to form a siloxane group). Many such compounds are commercially available.

One preferred silicon hydride is $R^5nSiH_{4-n}$ wherein each $R^5$ is independently alkyl containing 1 to 20 carbon atoms, aryl, chloro, bromo, alkoxy containing 1 to 4 carbon atoms, and acyloxy containing 1 to 6 carbon atoms, and n is 1, 2 or 3. In an especially preferred silicon hydride, each $R^5$ is independently methyl, ethyl, phenyl, methoxy, ethoxy, or chloro. Another preferred silicon hydride is $R^5_mH_{3-m}SiOSiR^5_mH_{3-m}$ wherein $R^5$ is as defined above and m is 0, 1, or 2. Especially preferred $R^5$ are as given above. Another preferred silicon hydride is a cyclic siloxane of the formula $(R^5_2SiO)_x(R^5_tH_{2-t}SiO)_y$, wherein $R^5$ is as defined above, x +y is 3, 4, or 5, y is an integer of one or more, x is 0, 1, 2, 3 or 4, and t is 0 or 1. Especially preferred $R^5$ groups are as defined above. Another preferred silicon hydride is a linear polysiloxane of the formula $R^5_3SiO(R^5_2SiO)_q(R^5_sH_{2-s}SiO)_rSiR^5_3$, wherein $R^5$ is as defined above, q is 0 or an integer of 1 or more, r is an integer of 1 or more, and each s is independently 0 or 1. Especially preferred R5 groups are as given above. In preferred linear polysiloxanes q r is about 5 to about 10,000, and it is more preferred if q+r is about 10 to about 1,000. For the linear polysiloxanes, it is more preferred if each R5 is methyl, ethyl or phenyl, and most preferred if each R5 is methyl. The linear polysiloxanes which are the products of the process have the formula $R^5_3SiO(R^5_2SiO)_1[R^5_sH_uSi(CH_2CH_2CFR^1R^2)_tO]_rSiR^5_3$, wherein $R^1$, $R^2$, $R^5$, q, r, and s are as defined as above, each t is independently 1 or 2, each u is independently 0 or 1, and s + t + u for any individual silicon atom is 2.

The process is carried out at a temperature of about 0° C. to about 200° C., preferably 20° C. to 60° C. Typical reaction times are about 1 hr to about 5 days. In order to prevent decomposition of starting materials and/or products it is preferred to carry out the process in the absence of water and oxygen, so it is convenient to use an inert atmosphere above the reaction, such as nitrogen. To bring the ingredients into contact with one another it is preferred if the reaction is agitated. Products can be isolated by known techniques, depending on the properties of the products, such as evaporation of solvent, distillation or filtration. Solvents may optionally be used in the process, so long as they don't react with any of the starting materials or products. Solvents should not have any active hydrogen atoms. When all of the Si-H groups in the silane are to be reacted, it has been found advantageous to use an excess of moles of alpha-fluorinated olefin to equivalents of silicon hydride ($\equiv$Si—H). Thus it is preferred if the ratio of moles of olefin to equivalents of silicon hydride is about 3:1 to about 1:3, and especially preferred if it is about 1.3:1 to about 1:1. The process also requires that a catalytically effective amount of the cobalt catalyst be present. A typically effective ratio of moles of cobalt catalyst to equivalents of silicon hydride is about 0.1:1 to about 0.0001:1, preferably 0.03:1 to 0.005:1, more preferably 0.01:1 to 0.005:1.

The hydrosilated low molecular weight products of the instant process are useful as monomers for polymerization and as chemical intermediates. The hydrosilated polymers are useful as lubricants, surface modifiers, chemically and solvent resistant elastomers and caulks, and for solvent resistant coatings.

The following materials are used in the Examples:
Darco® G-60 - Activated carbon available from EM Science, Gibbstown, NJ, USA.
Freon® 113 -1,1,2-trichloro-1,2,2-trifluoroethane, available from E. I. du Pont de Nemours & Co., Wilmington, DE USA
(Perfluoro-n-butyl)ethylene - Available as Zonyl® PFBE from DuPont
Trimethylsiloxy terminated polymethylsiloxanes were obtained from Huls America, Inc., Piscataway, NJ, USA

EXAMPLES

Example 1 reaction of $F(CF_2)_4CH=CH_2$ with $Me_3SiO(SIMEHO)_{14}SiMe_3$ and $Co_2(CO)_6[P(OMe)_3]_2$ Catalyst.

P(OMe)$_3$ (0.21 g, 0.169 mmol) and Co$_2$(CO$_8$ (0.030 g, 0.088 mmol) were stirred in 1 ml toluene (dried and distilled from CaH$_2$) for 30-45 min. in a drybox. Polyhydromethylsiloxane (2 ml, 0.033 mole SiH) and $F(CF_2)_4CH=CH_2$ (10 ml, 0.057 mole) were added to the catalyst solution and stirring continued for a few days. Small samples (~0.5 ml) were occasionally withdrawn, diluted with F-113, filtered through neutral Al$_2$O$_3$ and Darco G-60 and subjected to $^1$H NMR analysis to determine extent of the reaction. After 5 days at room temperature the reaction system was diluted with 30 ml F-113, filtered through neutral Al$_2$O$_3$ and Darco G-60, volatiles were stripped on a rotary evaporator and under high vacuum. Yield: 4.0 g (40%) blue, transparent, viscous oil. $^1$H NMR (F-113+CDCl$_3$):$\delta$0.1–0.3 (m, SiCH$_3$), 0.88 (m, SiCH$_2$—CH$_2$—CF$_2$, 84% relative to Si—CH$_3$), 2.14 (m, SiCH$_2$—CH$_2$—CF$_2$), 4.83 (s, SiH, 13% relative to Si—CH$_3$); $^{19}$FNMR (Freon® 113, CDCl$_3$ and Freon®11): —81.0 (t, 3F), —116.9 (m, 2F), —124.7 (m, 2F), —126.6 (m, 2F); $^{29}$Si NMR: 10.2 (m, OSI(CH$_3$)$_3$), —19.2 to —22.7 (m, OCH$_3$SiCH$_2$CH$_2$(CF$_2$)$_4$FO), —34.9 to —35.8 (OCH$_3$SiHO). Anal. found (calcd for Me$_3$SiO[SiMeCH$_2$CH$_2$(CF$_2$)$_4$FO]$_{15}$ SiMe$_3$): C, 27.00 (28.26); H, 2.61 (2.63), F, 53.72 (54.20), Si, 10.47 (10.14).

EXAMPLE 2

Reaction of $F(CF_2)_4CH=CH_2$ with $Me_3SiO(SiMeHO)_{14}SiMe_3$ and $Co_2(CO)_8$ Catalyst.

A mixture of Co$_2$(CO)$_8$ (6g, 17.6 mmole), polymethylhydrosiloxane (60 ml, 1.0 mole SiH) and $F(CF_2)_4$—CH=CH$_2$ (210 ml, 1.2 mole) in a drybox was stirred for 5 days at room temperature. The reaction system was washed several times with MeOH, the bottom layer was separated, diluted with Freon® 113, filtered through neutral Al$_2$O$_3$, silica and Darco G-60, volatiles stripped on a rotary evaporator and under high vacuum. Yield: 190g (64%), viscous, pinkish oil. $^1$H NMR (F-113 +CDC13): $\delta$0.1–0.4 (m, SiCH$_3$), 0.9 (m, Si—CH$_2$—CF$_2$—CF$_2$, 69% relative to Si—CH$_3$); 2.2 (m, SiL CH$_2$—CH$_2$—CF$_2$), 3.55 (s, Si-OCH$_3$), 4.85 (s, Si-H); $^{19}$F NMR (THF-d$_8$+F—11):—81.7 (t, 3F), —114 to —115 (br, minor), —116.5 (m, 2F), —124.3 (m, 2F), —126.3 (m, $^2$F); $^{29}$Si NMR (F-113+CDC13):10.2 (m, OSi(CH3)3), —21.6 (m, OCH$_3$SiCH2CH2(CF2)-4FO), —35.1 (m, OCH$_3$SiHO), —56 to —67 (broad, minor); GPC (THF): Mn=3,480, $M_w/M_n$=1.33 (vs PS).

EXAMPLE 3

Preparation of Me$_3$SiO(SiMeCH$_2$CH$_2$C$_4$F$_9$O)$_m$(SiMeC$_{15}$H$_{31}$O)$_n$SiMe$_3$ (m+n=14).

A mixture of Co$_2$(CO)$_8$ (16.5q, 48.8 mmol), polymethylhydrosiloxane (250 ml, 4.0 mole SiH), H(CH$_2$)$_{12-14}$CH=CH$_2$ (165 ml, 0.6 mole) and C$_4$F$_9$CH=CH$_2$ (610 ml, 3.5 mole) under nitrogen was stirred at 55° C. for 8 days. The reaction system was worked up according to the procedure described in Example 2. Yield: 750g (61%), transparent pinkish oil, viscosity: 1,290 cSt (100° F.). 130 cSt (210° F.); $^1$H NMR (F-113+CDCl$_3$): $\delta$0.2 (m, SiCH$_3$), 0.65 (m, Si—CH$_2$—CH$_2$—CH$_2$, (8.6% relative to Si—CH$_3$)), 0.8—1.0 (m, Si—CH$_2$—CH$_2$—CF$_2$ (80% relative to SiCH$_3$) and CH$_2$CH$_3$), 1.4 (m, CH$_2$—CH$_2$—CH$_2$), 2.0 (m, SiCH$_2$CH$_2$CF$_2$).

EXAMPLE 4

Preparation of —[—(CH$_2$)$_2$—(CF$_2$)$_4$—(CH$_2$)—(SiMe$_2$O)$_2$SiMe$_2$—]$_x$ A mixture of Co$_2$(CO)$_8$ (0.1 g, 0.29 mmol), HSiMe$_2$OSiMe$_2$OSiMe$_2$H (3.9 ml, 15.4 mmol), and CH$_2$=CH—(CF$_2$)$_4$—CH=CH$_2$ (3 ml, 16.4 mmol) in a drybox was stirred at rt for 4 days then heated at 60° C. for additional 10 h. Yield: 6g (81%), dark, very viscous oil. GPC (THF):$M_n$=6,560, $M_w/M_n$=1.71 (vs. PS), $^1$H NMR (THF-d$_8$): $\delta$0.1—0.3 (m, Si—CH$_3$), 0.9 (m, Si-—CH$_2$—CH$_2$—CF$_2$, 85% relative to Si—CH$_3$), 2.2 (m. Si—CH$_2$—CH$_2$—CF$_2$).

EXAMPLE 5

Preparation of (C$_8$F$_{17}$CH$_2$CH$_2$)$_2$Si(CH$_3$)Ph.

A mixture of H$_2$SiMePh (0.6 ml, 4.37 mmol), C$_8$F$_{17}$—CH=CH$_2$ (3 ml, 11.1 mmol), Co$_2$(CO)$_8$ (0.2 g, 0.58 mmol) and 0.3 ml decane (GC standard) in a drybox was stirred at rt for 24 hrs. The mixture was diluted with F-113, filtered through neutral $Al_2O_3$ and Darco G-60, volatiles stripped on a rotary evaporator and under high vacuum. Yield: 3 g (68%), clear oil. $^1H$ NMR (F-113+CDCl$_3$): δ0.2 (s, 3H), 0.9 (m, 4H), 1.9 (m, 4H), 7.2 (m, 5H); $^{19}F$ NMR (F−113+CDCl$_3$+F−11): −81.2 (t, 3F), −115.7 (m, 2F), −121.7 (m, 6F), −122.6 (m, 2F), −123.0 (m, 2F), −126.2 (m, 2F); MS [M+F]:

1H), 7.4 (m, 3H), 7.6 (m, 2H); MS [M+F]: Calc. 649.0656, Found 649,0606.

EXAMPLES 9-17

Hydrosilylation of $F(CF_2)_4CH=CH_2$ with $Me_3SiO(SiMeHO)_{14}SiMe_3$ in the presence of $Co_2(CO)_6(PX_3)_2{}^a$

| Example | Catalyst Co$_2$(CO)$_6$(PX$_3$)$_2$ | (mol/LX10$^3$) | Time (h) | Temp (°C.) | SiH Conv.$^b$ (%) | Yield of ≡SiCH$_2$CH$_2$(CF$_2$)$_4$F$^b$ (%) |
|---|---|---|---|---|---|---|
| 9 | P(n-Bu)$_3$ | (3.90) | 144 | RT | 75 | 67 |
|   |   | (7.80) | 144 | 60 | 100 | 75 |
| 10 | PEt$_3$ | (3.48) | 120 | RT | 89 | 69 |
|   |   | (6.96) | 72 | 60 | 100 | 74 |
| 11 | PPh$_2$Me | (4.64) | 120 | RT | 89 | 72 |
|   |   | (9.28) | 168 | 60 | 100 | 79 |
| 12 | PMe$_2$Ph | (4.65) | 66 | RT | 16 | 7 |
| 13$^c$ | PMe$_3$ | (4.65) | 66 | RT | 72 | 58 |
| 14 | P(OPh)$_3$ | (5.32) | 48 | RT | 20 | 16 |
| 15 | P(O-i-Pr)$_3$ | (4.66) | 120 | RT | 92 | 81 |
| 16 | P(OMe)$_3$ | (3.58) | 120 | RT | 94 | 86 |
| 17 | P(OMe)$_3$ | (3.58) | 19 | 60 | 38 | 32 |
|   |   |   | 44 | 60 | 40 | 34 |

$^a$F(CF$_2$)=CH$_2$ (4.14 mol/L), Me$_3$SiO(SiMeHO)$_{14}$SiMe$_3$ (3.03 SiH mol/L) in toluene.
$^b$Concentrations of SiH and SiCH$_2$CH$_2$(CF$_2$)$_4$F determined by $^1$H NMR relative to Si—CH$_3$.
$^c$In tetrahydrofuran.

Calc: 1033.0462, Found: 1033.0272.

EXAMPLE 6

Preparation of $C_6H_{13}SiH(CH_2CH_2C_4F_9)_2$

A mixture of $Co_2(CO)_8$ (0.2 g, 0.58 mmol), $C_4F_9CH=CH_2$ (4 ml, 22.7 mmol) and $C_6H_{13}SiH_3$ (1 ml, 6.19 mmol) was stirred in a drybox. Progress of the reaction was followed by GC. After 48 hrs. more $Co_2(CO)_8$ (0.2 g, 0.58 mmol) was added. After another 24 hrs. GC showed 78% of the desired product. The mixture was diluted with F-113, filtered through neutral $Al_2O_3$ and Darco G-60, volatiles stripped on a rotary evaporator and under high vacuum. Yield: 1.5 g (39%), brown solid, $T_M=24°$ C. (DSC). $^1H$ NMR: δ0.7 (m, 6H), 0.9 (t, 3H), 1.3 (m, 8H), 2.1 (m, 4H), 3.8 (m, 1H); MS [M+F]: Calc. 627.1187: Found 627.1118.

EXAMPLE 7

Preparation of $PhSiH(CH_2CH_2C_4F_9)_2$

A mixture of $Co_2(CO)_8$ (0.2g, 0.58 mmol), $C_4F_9CH=CH_2$ (4 ml, 22.7 mmol), $PhSiH_3$ (0.8 ml, 6.43 mmol) and F-113 (2.5 ml) was stirred in a drybox. After 3 days GC showed ~85% of the desired product. The reaction mixture was worked up according to the procedure described in Example 6. Yield: 2.5 g (65%), waxy solid, $T_M=17°$ C. (DSC). $^1H$ NMR (THF-d$_8$): δ1.2 (m, 4H), 2.2 (m, 4H), 4.6 (brs, 1H), 7.4 (m, 3H), 7.6 (m, 2H).

EXAMPLE 8

Preparation of $Ph_2SiHCH_2CH_2C_8F_{17}$

A mixture of $h_2SiH_2$ (0.75 ml, 4.08 mmol), $C_8F_{17}CH=CH_2$ (3 ml, 11.1 mmol), $Co_2(CO)_8$ (0.1 g, 0.29 mmol) and 0.3 ml decane (GC standard) was stirred in a drybox. After 1.5 hrs. GC showed 92% of the desired product. The reaction mixture was worked up according to the procedure described in Example 6. The product was partially transformed into $Ph_2Si(OCH_3)CH_2CH_2C_8F_{17}$ when dissolved in MeOH during work up. Yield: 1.2 g (48%), brown oil. $^1H$ NMR (F-113+CDCl3): δ0.9 (m, 2H), 2.2 (m, 2H), 4.9 (brs,

EXAMPLE 18

Reaction of $F(CF_2)_nCH=CH_2$, where n=6, 8, 10, 12 with $Me_3SiO(SiMeHO)_{75}SiMe_3$ and $Co_2(CO_8)$ Catalyst.

A mixture of $Co_2(CO)_8$ (6 g, 17.6 mmol), polymethylhydroxiloxane (70 ml, 1.1 mole SiH), $F(CF_2)_nCH=CH_2$ (350 ml, 1.3 mole) and F-113 (475 ml) in a drybox was stirred at rt for 24 hrs. The reaction mixture was worked up according to the procedure described in Example 2. Yield: 489 g (82%), white solid, $T_M=40°$ C. (DSC). $^1H$ NMR (F-113+CDCl$_3$): δ0.1-0.3 (m, SiCH$_3$),0.9 (m, SiCH$_2$CH$_2$CF$_2$, 71% relative to SiCH$_3$), 2.2 (m, SiCH$_2$CH$_2$CF$_2$), 3.6 (s, SiOCH$_3$, 5.5% relative to SiCH$_3$), 4.9 (s, SiH, 12% relative to SiCH$_3$).

What is claimed is:

1. A process for the hydrosilation of alpha-fluorinated olefins, comprising, contacting a silicon hydride with an olefin of the formula $H_2C=CHCFR^1R^2$ and a catalytically effective amount of catalyst of the formula $Co_2(CO)_{8-z}L_z$, wherein:
   $R^1$ is fluorine or perfluorohydrocarbyl;
   $R^2$ is fluorine, hydrogen, hydrocarbyl, or substituted hydrocarbyl;
   z is 0 or an integer of 1 to 7;
   each L is independently CO, $PR^3{}_3$ or $P(OR^4)_3$;
   $R^3$ is hydrocarbyl;
   $R^4$ is hydrocarbyl; and provided that when L is $PR_3{}3$ only one or two of $R^3$ is aryl.

2. The process as recited in claim wherein $R^1$ is perfluoroalkyl and $R^2$ is fluorine.

3. The process as recited in claim 2 wherein $R^1$ is perfluoro-n-alkyl containing 2 to 20 carbon atoms and $R^2$ is fluorine.

4. The process as recited in claim 1 wherein $R^2$ is -hydro or -haloperfluoro-n-alkyl, and $R^1$ is fluorine.

5. The process as recited in claim 1 wherein z is 0 or 2.

6. The process as recited in claim 1 wherein each $R^3$ and each $R^4$ is independently alkyl containing 1 to 6 carbon atoms, or phenyl.

7. The process as recited in claim 6 wherein each $R^3$ and each $R^4$ is independently phenyl or methyl.

8. The process as recited in claim 2, 3, 4, 5, 6, or 7 wherein the silicon hydride is $R^5{}_nSiH_{4-n}$, $R^5{}_mH_{3-m}SiOSiR^5{}_mH_{3-m}$, a cyclic siloxane of the formula $(R^5{}_2SiO)_x(R^5{}_tH_{2-t}SiO)_y$, or a linear polysiloxane of the formula $R^5{}_3SiO(R^5{}_2SiO)_q(R^5{}_sH_{2-s}SiO)_rSiR^5{}_3$, wherein:
- each $R^5$ is independently alkyl containing 1 to 20 carbon atoms, aryl, chloro, bromo, alkoxy containing 1 to 4 carbon atoms, or acyloxy containing 1 to 6 carbon atoms;
- n is 1, 2, or 3;
- m is 0, 1, or 2.
- x+y is 3, 4, or 5,
- y is an integer of one or more;
- t is 0 or 1;
- q is 0 or an integer of 1 or more;
- r is an integer of 1 or more; and
- each s is independently 0 or 1.

9. The process as recited in claim 1 wherein the silicon hydride is $R^5{}_nSiH_{4-n}$, $R^5{}_mH_{3-m}SiOSiR^5{}_mH_{3-m}$, a cyclic siloxane of the formula $(R^5{}_2SiO)_x(R^5{}_tH_{2-t}SiO)_y$, or a linear polysiloxane of the formula $R^5{}_3SiO(R^5{}_2SiO)_q(R^5{}_sH_{2-s}SiO)_rSiR^5{}_3$, wherein:
- each $R^5$ is independently alkyl containing 1 to 20 carbon atoms, aryl, chloro, bromo, alkoxy containing 1 to 4 carbon atoms, or acyloxy containing 1 to 6 carbon atoms;
- n is 1, 2, or 3;
- m is 0, 1, or 2.
- x+y is 3, 4, or 5,
- y is an integer of one or more;
- t is 0 or 1;
- q is 0 or an integer of 1 or more;
- r is an integer of 1 or more; and
- each s is independently 0 or 1.

10. The process as recited in claim 9 wherein each $R^5$ is independently methyl, ethyl, phenyl, methoxy, ethoxy, or chloro.

11. The process as recited in claim 9 wherein q+r is about 5 to about 10,000.

12. The process as recited in claim 11 wherein q+r is about 10 to about 1,000.

13. The process as recited in claim 1, 2, 3, 4, 5, 6, 7, or 9 carried out at a temperature of about 0° C. to about 200° C.

14. The process as recited in claim 13 carried out at a temperature of about 20° C. to about 60° C.

15. The process as recited in claim 1, 2, 3, 4, 5, 6, 7 or 9 wherein the ratio of moles of olefin to equivalents of silicon hydride is about 3:1 to about 1.3.

16. The process as recited in claim 15 wherein said ratio is about 1.3:1 to about 1:1.

17. The process as recited in claims 1, 2, 3, 4, 5, 6, 7 or 9 wherein the ratio of moles of cobalt catalyst to equivalents of silicon hydride is about 0.1:1 to about 0.0001:1.

18. The process as recited in claim 17 wherein said ratio is 0.01:1 to 0.005:1.

* * * * *